US009442018B2

(12) United States Patent
Sreedharan Nair et al.

(10) Patent No.: US 9,442,018 B2
(45) Date of Patent: Sep. 13, 2016

(54) METHOD AND ALGORITHM FOR SELF-LEARNING/AUTO-COMMISSIONING BY MULTIPLE SENSOR ELEMENTS FOR OUTDOOR LIGHTING APPLICATION

(71) Applicant: KONINKLIJKE PHILIPS N.V., Eindhoven (NL)

(72) Inventors: Biju Kumar Sreedharan Nair, Veldhoven (NL); Roger Peter Anna Delnoij, Lommel (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 21 days.

(21) Appl. No.: 14/372,764

(22) PCT Filed: Jan. 10, 2013

(86) PCT No.: PCT/IB2013/050215
§ 371 (c)(1),
(2) Date: Jul. 17, 2014

(87) PCT Pub. No.: WO2013/108158
PCT Pub. Date: Jul. 25, 2013

(65) Prior Publication Data
US 2015/0014539 A1    Jan. 15, 2015

Related U.S. Application Data

(60) Provisional application No. 61/588,826, filed on Jan. 20, 2012.

(51) Int. Cl.
| | | |
|---|---|---|
| *G01J 5/00* | (2006.01) | |
| *G01J 5/08* | (2006.01) | |
| *H05B 37/02* | (2006.01) | |
| *G01N 21/35* | (2014.01) | |
| *G08B 13/191* | (2006.01) | |
| *G08B 29/18* | (2006.01) | |

(52) U.S. Cl.
CPC ............ *G01J 5/0806* (2013.01); *G01N 21/35* (2013.01); *H05B 37/0227* (2013.01); *G08B 13/191* (2013.01); *G08B 29/185* (2013.01); *Y02B 20/44* (2013.01); *Y02B 20/72* (2013.01)

(58) Field of Classification Search
CPC . G01J 5/0806; G01N 21/35; H05B 37/0227; Y02B 20/72; Y02B 20/44; G08B 13/191; G08B 29/185

USPC ........................................................ 250/340
See application file for complete search history.

(56) References Cited

U.S. PATENT DOCUMENTS

| | | | | |
|---|---|---|---|---|
| 5,134,292 A | | 7/1992 | Segawa | |
| 5,428,388 A | * | 6/1995 | von Bauer | H04N 7/186 348/155 |

(Continued)

FOREIGN PATENT DOCUMENTS

EP    1398742 A1    3/2004

OTHER PUBLICATIONS

"Remguard & Optex Drive Down False Activation", RemGuard Visual Management, vol. 1, Issue 1, Jun. 2006, pp. 1-6, www.optex-europe.com.

*Primary Examiner* — David Porta
*Assistant Examiner* — Gisselle Gutierrez
(74) *Attorney, Agent, or Firm* — Meenakshy Chakravorty

(57) ABSTRACT

The invention relates to a method of controlling a passive infrared (PIR) sensor, said sensor controlling if an electrical device is on or off, wherein said PIR sensor has at least two sensor elements, each having a lens focusing IR onto them, control electronics comprising of at least one processing unit and one memory, wherein the at least two sensors cover adjacent cover areas, wherein information of detected presence from said at least two sensor elements are used to decrease false triggers by using the time period between subsequent presence detections, and identification of each of said at least two PIR sensor elements. The invention further relates to a method of controlling a passive infrared (PIR) sensor, said sensor controlling if an electrical device is on or off, wherein said PIR sensor has two or more sensor elements, each having a lens focusing IR onto them, control electronics comprising of at least one processing unit and one memory, wherein two or more sensors cover different sequentially adjacent cover areas, wherein the sensor elements have a threshold for IR detection above which threshold a positive signal of presence is provided from the sensor element, said method comprising the step of provide a signal (Pan) if all sensor elements provide a positive signal of presence during a time period shorter than a predetermined time period (T3), and if ($P_{all}$) is detected a predetermined number of times within a second predetermined time period (T4), increase said threshold by a predetermined amount.

6 Claims, 4 Drawing Sheets

(56) References Cited

U.S. PATENT DOCUMENTS

| | | | | |
|---|---|---|---|---|
| 5,473,311 A | * | 12/1995 | Hoseit | G08B 29/183 340/522 |
| 6,313,462 B1 | * | 11/2001 | Matsuda | G01J 5/14 250/338.3 |
| 6,791,458 B2 | | 9/2004 | Baldwin | |
| 7,411,489 B1 | * | 8/2008 | Elwell | G08B 13/1645 307/116 |
| 2002/0175815 A1 | | 11/2002 | Baldwin | |
| 2009/0174552 A1 | * | 7/2009 | Soccoli | G01J 1/02 340/541 |
| 2010/0102962 A1 | * | 4/2010 | Hick | H05B 37/0227 340/541 |
| 2010/0109934 A1 | | 5/2010 | Drake | |
| 2010/0201527 A1 | | 8/2010 | Jensen | |
| 2011/0109455 A1 | * | 5/2011 | Bergman | G08B 29/046 340/568.5 |
| 2011/0109456 A1 | * | 5/2011 | Bergman | G08B 13/2402 340/568.5 |
| 2013/0002147 A1 | * | 1/2013 | Lagutko | H05B 37/0218 315/158 |
| 2015/0137621 A1 | * | 5/2015 | Emby | G05B 11/01 307/140 |

* cited by examiner

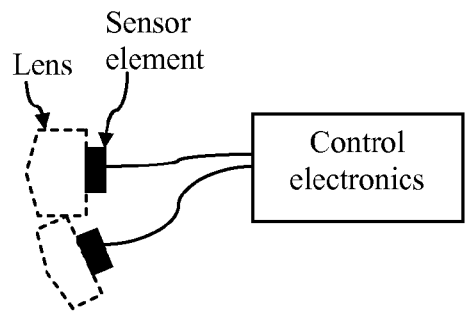
Fig. 1 – Prior art
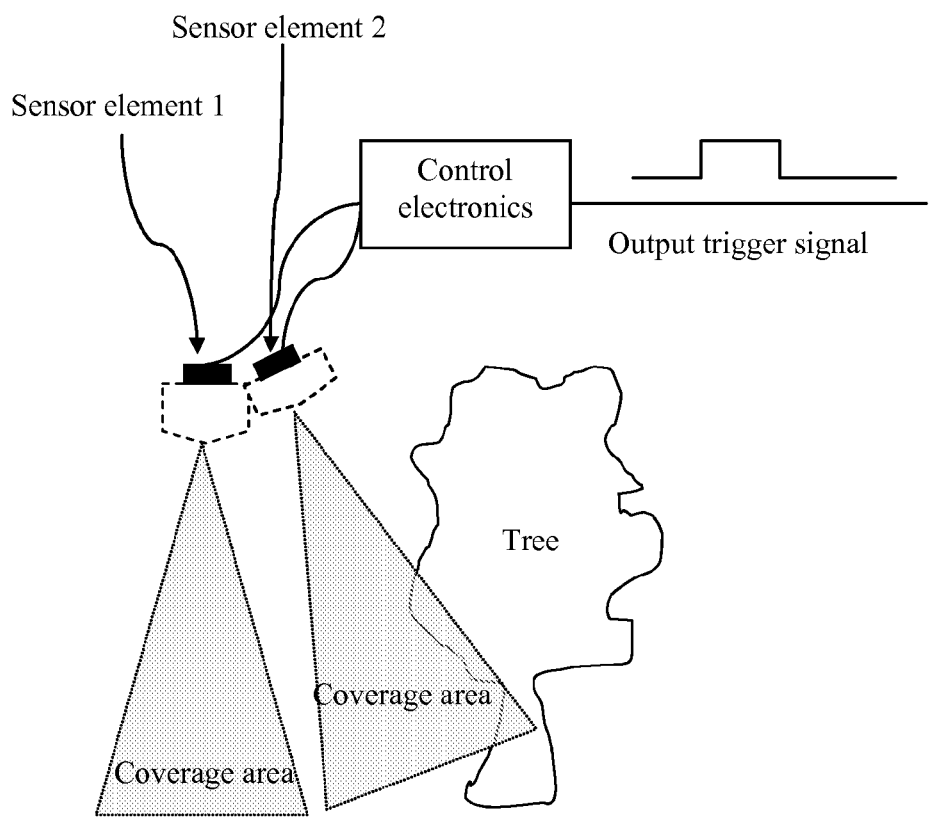
Fig. 2 – prior art

US 9,442,018 B2

METHOD AND ALGORITHM FOR SELF-LEARNING/AUTO-COMMISSIONING BY MULTIPLE SENSOR ELEMENTS FOR OUTDOOR LIGHTING APPLICATION

CROSS-REFERENCE TO PRIOR APPLICATIONS

This application is a U.S. national stage application under 35 U.S.C. §371 of International Application No. PCT/IB2013/050215, filed on Jan. 10, 2013, which claims priority benefit under 35 U.S.C. §119(e) of U.S. Provisional Application No. 61/588,826 filed on Jan. 20, 2012, the contents of which are herein incorporated by reference.

FIELD OF THE INVENTION

The present invention relates generally to a method of controlling a passive infrared (PIR) sensor. More particularly, the present invention relates to a method of controlling a passive infrared (PIR) sensor as defined in the introductory parts of claim 1 and 5.

BACKGROUND OF THE INVENTION

The most mature and widely accepted presence detection technology is based on passive infrared (PIR) detection from human beings. These sensors are relatively low cost but are at the same time vulnerable for false triggers. False triggers may be false positive and false negative. False positive is when the sensor is triggered when nobody is present and false negative is when the sensor does not detect when somebody is present. A typical PIR sensor consists of lens to focus infrared (IR) energy onto the sensor element and control electronics to make decision on the presence detection/absence detection. FIG. 1 shows a multi-sensor system with multiple lens systems. The multiple sensors cover different sectors and increase the detection range and sensitivity. In those multi-element sensors, when one element is triggered by presence of a human being, the sensor outputs a trigger signal which in turn switches on a light source.

A false positive trigger scenario is shown in FIG. 2. A nearby object, e.g. a tree is moved by some means, e.g. by the wind. The sensor detects IR movement and may perform a false positive trigger signal. The false trigger signal in this case is generated by a difference in foreground and background, where the tree is the foreground and, e.g., a street or a building is the background. If the tree moves, different parts of the background will be sensed which can lead to a false positive trigger signal.

The false positive trigger scenarios shown in FIG. 2 are typically depending on the weather, and the environment or more precisely the contrast in background. These false positive triggers are difficult to predict and usually occur during longer periods at the same location.

False triggers of PIR-sensors will switch on lighting and/or other equipment consuming energy, which is both expensive and detrimental to the environment.

There is thus a need to provide a more robust PIR sensor that will not give false positive trigger signals from unintended objects within a PIR sector of a PIR sensor having multiple sensors. This should be achieved without adding too much cost to the sensor, since the PIR-sensors market is price sensitive due to the vast and increasing number of PIR sensors used in society.

SUMMARY OF THE INVENTION

It is an object of the present invention to improve the current state of the art, to solve the above problems, and to provide an improved passive infrared sensor that will self-adapt to its surroundings to avoid false positive triggers. These and other objects are achieved by a method of controlling a passive infrared (PIR) sensor, said sensor controlling if an electrical device is on or off, wherein said PIR sensor has at least two sensor elements, each having a lens focusing IR onto them, control electronics comprising at least one processing unit and one memory, wherein the at least two sensors cover adjacent cover areas, wherein information of detected presence from said at least two sensors are used to decrease false triggers by using time between subsequent presence detections, and identification of the PIR sensor detecting presence.

By correlating different presence detection occurrences it is possible to detect false trigger events and raise the threshold for detection if false triggers are suspected. By avoiding false triggers, energy of connected electrical equipment is saved. By self learning from the actual events, the PIR-sensor will become more robust over time.

More specifically the method will perform the following steps when presence is detected: saving the time T1 and identification of the first sensor element S1 detecting the presence, sending a switch-on signal to the attached electrical device, setting a first delay time D1, if no presence is detected during the delay, sending a switch-off signal to the attached electrical device if presence is detected by a second sensor element S2 during at a time T2 that is less than a predetermined time period M, increasing the switch-off delay time to a second delay time D2, being greater than first delay time D1.

If the trigger event of only one event is a false positive trigger signal, the shorter delay D1, will make sure that not too much energy is wasted. If, on the other hand, another sector, i.e. another sensor, detects presence, it is less likely to be a false positive trigger signal and the delay time can be set longer to not cause the electrical device, e.g. a lighting device, to turn off when a human is present in the area covered by the PIR sensor.

The method of controlling a passive infrared (PIR) sensor may further comprise the steps of increasing the threshold for detection of a sensor after a predetermined number of occurrences where presence is not detected by a second sensor within said time period M, and save said increased threshold for the particular sensor to said memory.

If one sensor has reoccurring positive trigger signals without other sectors detecting presence, it is likely that the trigger signals are false and are due to, e.g., moving foreground objects as a tree moving in the wind. The threshold for giving a positive trigger signal is then increased for that sensor to avoid false positive trigger signals in the future, saving energy due to false triggers.

The second time delay D2 is a default value of a time delay that is greater than the first time delay D1. D1, which is the delay time when only one sector has detected presence, is held shorter due to the increased risk of the signal being a false positive trigger signal. In that way a false trigger signal will turn on the electrical equipment for a shorter time, saving energy due to false trigger signals.

The invention further relates to a method of controlling a passive infrared (PIR) sensor, said sensor controlling if an electrical device is on or off, wherein said PIR sensor has at least two sensor elements, each having a lens focusing IR onto them, control electronics comprising at least one processing unit and one memory, wherein the at least two sensors cover different sequentially adjacent cover areas, wherein the sensor elements have a threshold for IR detection above which threshold a positive signal of presence is provided from the sensor element, said method comprising the step of providing a signal $P_{all}$ if all sensor elements provide a positive signal of presence during a time period shorter than a predetermined time period T3, and if $P_{all}$ is detected a predetermined number of times within a second predetermined time period T4, increasing said threshold by a predetermined amount.

When all PIR-sensors detect presence at the same time, e.g. during a time span T3 of 0.25 seconds, it is likely that the sensor device has moved and not objects in its cover area. The inventive method will then increase the threshold of each sensor element to avoid false triggers due to movements of the PIR-sensor device in the future. In this situation light can be switched ON with a smaller switch-off delay, D1 to save energy.

In the case that each sensor has its own threshold above which a positive signal of presence is provided from the sensor element, said increase by a predetermined amount is added to each threshold for each sensor element respectively.

The increase of the threshold by a predetermined amount may be a relative predetermined amount increasing each threshold for each sensor element relative to the current threshold of the sensor.

To summarise the advantages of the invention, it provides robust presence detection with multiple sensor elements where the system becomes self-learning by means of analysis of the signals from different PIR elements which enables auto-commissioning, energy reduction in case of false-triggers, and less annoyance of end-users.

The extra sensitivity is obtained by using multiple sensors and multiple optics. From this low resolution spatial information is obtained that is used to do automatic masking and filtering as described by the method variants above. The reduced false triggers will increase energy savings and provide a more predictable performance.

The basic concept of the invention is that the sensor detects frequent recurring movements within one zone only (i.e. no trajectory), to increase the threshold for false positive trigger signals and thereby automatic filter and mask the covered area. If all sensors frequently see movement simultaneously in all zones, the threshold is increased and a filter for a moving sensor device, also called pole swing, is achieved.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein:

FIG. 1 is a schematic drawing of a PIR sensor device according to prior art.

FIG. 2 is a schematic drawing of the cover area of a PIR sensor device according to prior art.

DETAILED DESCRIPTION OF THE EMBODIMENTS

Figure 3:
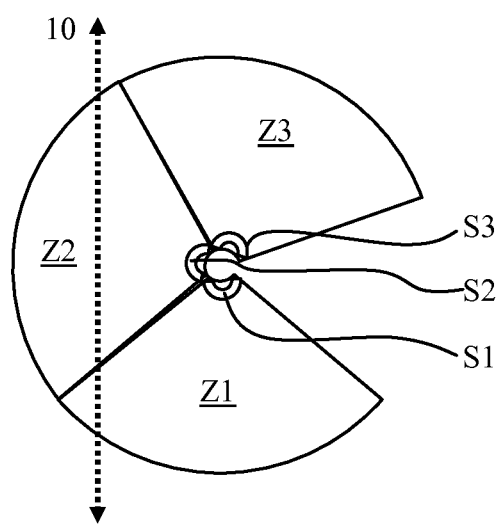
FIG. 3 is a schematic drawing of a PIR sensor device having three sectors.

A typical sensor with three sensor elements S1-S3 can have a detection coverage area as shown in FIG. 3, where each sensor has a cover area or cover zone marked by Z1-Z3. Typically when a person or a vehicle is passing by the sensor at least two sensors will see the movement as marked in the FIG. 3 by the arrow 10.

Figure 4:
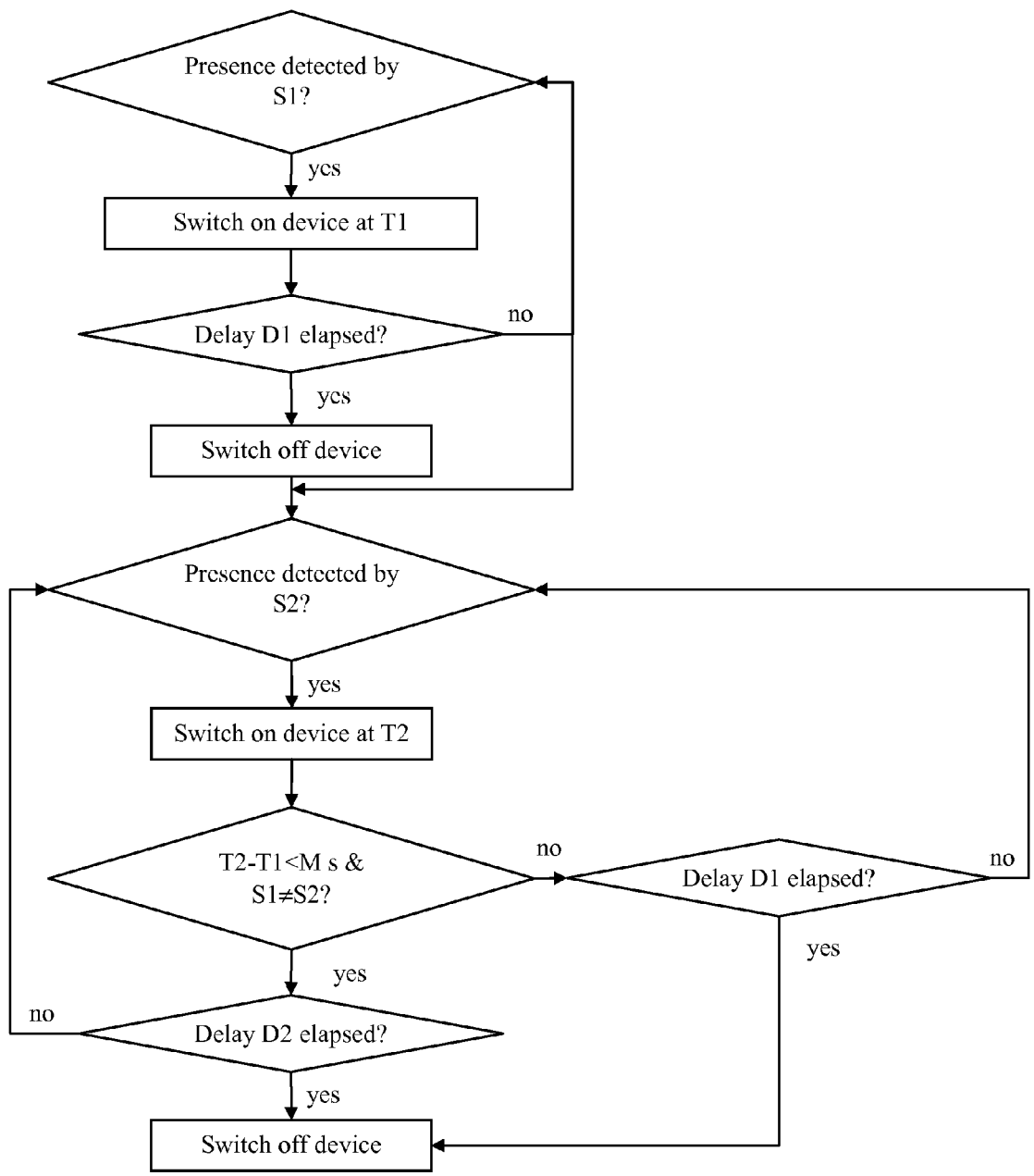
FIG. 4 is a flow chart describing the inventive method reducing false triggers due to external objects.

A control algorithm with N number of sensors (S1:SN) can be thought of as shown in FIG. 4. By checking the conditions (T2−T1<) & S1≠S2, it can be checked whether the detections are always happening in one zone, indicating that there is a fixed moving object like trees, infrared reflections, etc, falsely triggering the sensor. If different sensor elements are triggered within a limited time interval, e.g. in 10 seconds, there is a higher probability that it is true presence which means switch-off delay should be the default value D2. In case, presence detection is given only from one zone or sensor element for a long period of time, the switch-off delay D1 is still smaller than D2, meaning that energy miss-usage from false trigger will be reduced.

The steps in the method shown in FIG. 4 are as follows, If presence is detected by a sensor S1, an electrical device, e.g. a lighting device or ventilation device, is switched on at time T1. If delay D1 has passed without detected presence, the device is switched off again. If presence is detected by a second sensor S2, the device is switched on again at time T2. If presence is detected by the second sensor before the delay D1 has ended, it may omit the signal to switch on the device, but may also send it anyway to simplify the equipment. If it is determined that the time T2, when the second sensor S2 detected presence, is within a predetermined time period M from the last triggered event from the other sensor S1, the delay for switching off is increased from D1 to D2, since it is more likely that the detection is a true presence when presence has been detected in two sectors.

When continuous positive trigger signals are observed in one particular zone, threshold of detection can be increased to reduce false positive trigger signals.

Figure 5:
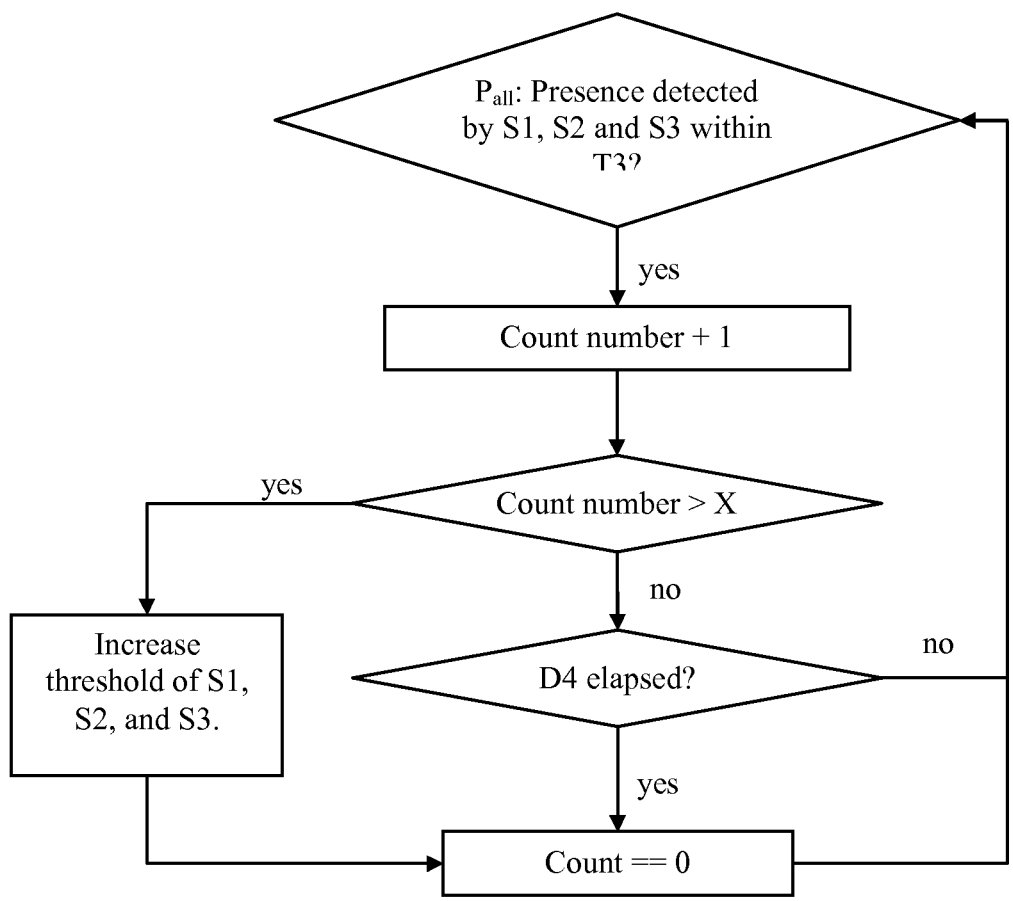
FIG. 5 is a flow chart describing the inventive method of reducing false triggers due to movements of the sensor.

Additionally, and referring to FIG. 5, the sensor includes an algorithm that monitors if all detections occur at once. If this happens frequently, then it is unlikely a valid detection, but instead due to motion of the entire sensor (e.g. pole swinging when the sensor is placed on a pole). If S2, S2, and S3 all have detection of presence during the predetermined time period T3, e.g. 0.25 sec, and this occurs a predetermined number of times X within a predetermined time period D4, e.g. 5 times during 5 minutes, presence will not be detected or a higher detection threshold will be set for the sensors S1, S2, and S3.

The present invention is applicable for lighting controls for outdoor and indoor that use PIR sensors for presence detection.

It is understood that other variations in the present invention are contemplated and in some instances, some features of the invention can be employed without a corresponding use of other features. E.g. may the electrical equipment connected to the sensor according to the invention be any kind of electrical equipment that is desired to be switched on or off at the presence of humans or animals. Accordingly, it is appropriate that the appended claims be construed broadly in a manner consistent with the scope of the invention.

The invention claimed is:

1. A method of controlling a passive infrared sensor, said sensor controlling whether an electrical device is switched on or off, and comprising at least two sensor elements, each sensor element having a lens for focusing IR onto itself, the method comprising the steps of:

saving a time and an identification of a first sensor element detecting the presence, sending a switch-on signal to said electrical device, setting a switch off delay duration to a first delay duration, determining if no presence is detected during the first delay duration, and sending a switch-off signal to said electrical device if no presence is detected during the first delay duration, and in response to determining that presence is detected by a second sensor element before the first delay duration has ended and during a time period that is less than a predetermined time period from a last triggered event from the first sensor element, increasing the switch off delay duration to a second delay duration that is greater than the first delay duration such that the switch-off signal is sent to said electrical device in response to determining that no presence is detected during the second delay duration, wherein information of detected presence from said at least two sensor elements are used to decrease false triggers.

2. The method of controlling a passive infrared sensor according to claim 1, further comprising the steps of increasing the threshold for detection of a sensor after a predetermined number of occurrences where presence is not detected by a second sensor within said predetermined time period, and saving said increased threshold for the particular sensor to a memory.

3. The method of controlling a passive infrared sensor according to claim 1, wherein the second delay duration is a default value and the first delay duration is a shortened delay duration.

4. A method of controlling a passive infrared sensor, said sensor controlling whether an electrical device is switched on or off, and having two or more sensor elements, each having a lens focusing IR onto itself, wherein each of the sensor elements have a threshold for IR detection above which a positive signal of presence is provided from the sensor element, said method comprising the steps of:

providing a signal in response to determining that all sensor elements provide the positive signal of presence during a time period shorter than a predetermined time period, and increasing said threshold for IR detection by a predetermined amount in response to determining that all sensor elements provide the positive signal of presence a predetermined number of times within a second predetermined time period.

5. A method of controlling a passive infrared sensor according to claim 4, wherein each sensor element has its own threshold above which the positive signal of presence is provided from the sensor element, wherein said increase by a predetermined amount is added to each threshold for each sensor element respectively.

6. A method of controlling a passive infrared sensor according to claim 5, wherein said increase of the threshold by a predetermined amount is a relative predetermined amount increasing each threshold for each sensor element relative to the current threshold of the sensor.

* * * * *